(12) United States Patent
Bernstein et al.

(10) Patent No.: US 8,142,211 B2
(45) Date of Patent: *Mar. 27, 2012

(54) APPARATUS FOR PREVENTING ELECTRICAL SHOCK IN DEVICES

(75) Inventors: Daniel M. Bernstein, El Granada, CA (US); R. Curtis Jennewine, San Francisco, CA (US); Charlene A. Haley, LaBelle, FL (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,857

(22) Filed: Jun. 1, 2010

(65) Prior Publication Data

US 2011/0133698 A1 Jun. 9, 2011

Related U.S. Application Data

(63) Continuation of application No. 12/200,591, filed on Aug. 28, 2008, now Pat. No. 7,946,866.

(51) Int. Cl.
*H01R 13/44* (2006.01)

(52) U.S. Cl. ......... 439/135; 439/373; 439/134; 439/149

(58) Field of Classification Search .................. 439/131, 439/133–135, 149, 373, 909
See application file for complete search history.

(56) References Cited

U.S. PATENT DOCUMENTS

| | | | |
|---|---|---|---|
| 3,811,104 A | 5/1974 | Caldwell | |
| 4,126,224 A | 11/1978 | Laauwe et al. | |
| 4,662,697 A * | 5/1987 | Moses | 439/148 |
| 4,911,344 A | 3/1990 | Kahler | |
| 4,957,831 A | 9/1990 | Meredith et al. | |
| 5,301,494 A | 4/1994 | Peot et al. | |
| 5,397,243 A * | 3/1995 | MacMurdo, Sr. | 439/136 |
| 5,582,180 A | 12/1996 | Manset et al. | |
| 5,701,232 A | 12/1997 | Tang et al. | |
| 5,708,247 A | 1/1998 | McAleer et al. | |
| 6,743,635 B2 | 6/2004 | Neel et al. | |
| 6,793,509 B2 | 9/2004 | Chen | |
| 6,881,578 B2 | 4/2005 | Otake | |
| 6,908,008 B2 | 6/2005 | Pugh | |
| 7,041,468 B2 | 5/2006 | Drucker et al. | |
| 7,172,728 B2 | 2/2007 | Otake | |
| 7,337,918 B2 | 3/2008 | Fowler et al. | |
| 7,488,216 B2 * | 2/2009 | Cho | 439/638 |
| 7,553,062 B2 | 6/2009 | Spartano et al. | |
| 2005/0169810 A1 | 8/2005 | Hagen et al. | |
| 2007/0179358 A1 | 8/2007 | Perez | |

(Continued)

FOREIGN PATENT DOCUMENTS

EP 1460727 9/2004

(Continued)

OTHER PUBLICATIONS

U.S. Appl. No. 12/200,591, Office Action mailed Aug. 26, 2010.

(Continued)

*Primary Examiner* — Tho D Ta
(74) *Attorney, Agent, or Firm* — Jackson & Co., LLP (57) ABSTRACT

A device for preventing electrical shock from a device with electrical interfaces. A shutter or other barrier associated with the device that physically prevents access or contact to one of the electrical interfaces while another electrical interface is in use.

20 Claims, 9 Drawing Sheets

U.S. PATENT DOCUMENTS

| | | |
|---|---|---|
| 2008/0099332 A1 | 5/2008 | Scott et al. |
| 2008/0128420 A1 | 6/2008 | Wang |
| 2010/0053851 A1 | 3/2010 | Bernstein et al. |
| 2010/0120276 A1* | 5/2010 | White .......................... 439/148 |

FOREIGN PATENT DOCUMENTS

| | | |
|---|---|---|
| WO | WO-2008/082987 | 7/2008 |
| WO | WO-2008/119648 | 10/2008 |
| WO | WO-2010/024971 | 3/2010 |

OTHER PUBLICATIONS

PCT Application No. PCT/US2009/050281, International Search Report mailed Nov. 27, 2009.

PCT Application No. PCT/US2009/050281, International Preliminary Report on Patentability and Written Opinion of the International Searching Authority mailed Mar. 10, 2011.

U.S. Appl. No. 12/200,591, Notice of Allowance mailed Jan. 10, 2011.

U.S. Appl. No. 12/200,591, Notice of Allowance mailed Jan. 28, 2011.

U.S. Appl. No. 12/791,847, Notice of Allowance mailed Jul. 27, 2011.

U.S. Appl. No. 12/791,847, Office Action mailed Jan. 7, 2011.

U.S. Appl. No. 12/791,847, Office Action mailed May 13, 2011.

U.S. Appl. No. 12/791,847, Office Action mailed May 2, 2011.

U.S. Appl. No. 12/791,849, Notice of Allowance mailed Jul. 28, 2011.

U.S. Appl. No. 12/791,849, Office Action mailed Jan. 7, 2011.

U.S. Appl. No. 12/791,849, Office Action mailed May 2, 2011.

U.S. Appl. No. 12/791,852, Notice of Allowance mailed Aug. 5, 2011.

U.S. Appl. No. 12/791,852, Office Action mailed Jan. 7, 2011.

U.S. Appl. No. 12/791,852, Office Action mailed May 2, 2011.

U.S. Appl. No. 12/791,855, Notice of Allowamce mailed Aug. 25, 2011.

U.S. Appl. No. 12/791,855, Office Action mailed Mar. 23, 2011.

U.S. Appl. No. 12/791,858, Notice of Allowance mailed Aug. 23, 2011.

U.S. Appl. No. 12/791,858, Office Action mailed Apr. 26, 2011.

* cited by examiner

APPARATUS FOR PREVENTING ELECTRICAL SHOCK IN DEVICES

RELATED APPLICATIONS

The present application is a continuation application of U.S. patent application Ser. No. 12/200,591 filed Aug. 28, 2008, entitled "Apparatus for Preventing Electrical Shock in Devices", the disclosure of which is incorporated herein in its entirety by reference for all purposes.

BACKGROUND OF THE INVENTION

1. The Field of the Invention

Embodiments of the invention generally relate to preventing users from receiving electrical shocks from operating medical devices. More specifically, embodiments of the invention relate to systems and methods for preventing electrical shock or reducing a risk of electrical shock from devices that analyze analytes.

2. The Relevant Technology

Diabetes is a disease that afflicts many people. Fortunately, much has been learned about the disease and today, diabetes can often be managed quite successfully. Managing diabetes often includes attention to both diet and exercise. It is also advisable to monitor blood glucose levels. Blood glucose levels can provide valuable information that contributes to the effective management of diabetes.

Monitoring blood glucose levels can be performed several times a day. Each time, a user typically draws a small sample of blood that is placed on a test strip. A measuring device analyzes the blood sample and provides a measurement of the person's blood glucose level from the blood sample.

In order to monitor or measure the glucose level of the blood sample, the measurement device may provide an electrical interface (e.g. port) that is constructed to receive a test strip and electrically connect with the test strip. This electrical interface is often exposed to the environment, including to the user of the measurement device. Similarly, the measurement device may have other electrical interfaces that may be used to connect the measurement device to a computer or to recharge an internal battery.

Measurement devices that allow access to electrical circuits can, in some situations, give a user an electrical shock if the user closes the circuit. More specifically, the electrical circuits of various measurement devices that are accessible via the port used to receive a test strip may be electrically connected to the port used to link or connect the measurement device to a computer or to recharge an internal battery.

For safety reasons, it is sometimes necessary to prevent the measurement device from being electrically connected to external equipment such as a computer or power supply when the measurement device is in contact with the user's body. The proximity of these electrical interfaces and their use can result in harm to the device and/or to the user. For example, the user of a measurement device may receive an electrical shock from the device if a circuit is inadvertently closed by the user. This could potentially occur, for example, when a user performs a finger stick test while the device is recharging or uploading data to a computer. In other words, current can flow to or from the external device through the person when they are "connected" to the measurement device.

BRIEF SUMMARY OF THE INVENTION

These and other limitations are overcome by embodiments of the invention, which relate to preventing electrical shock in devices including devices used to analyze analytes. Embodiments of the invention include physical barriers that prevent more than one electrical interface or port from being used at the same time. A physical barrier is configured to effectively cover one port such that the covered port cannot come into contact with the environment including the user while the other port is in use.

In an embodiment, the measurement device prevents electrical shocks related to use of ports on the measurement device and includes an enclosure that is formed in one end of the device's case or housing. The ports of the device are typically accessible through the enclosure. A shutter is disposed within the enclosure and is moveable within the enclosure to selectively cover one of the ports.

In certain embodiments, the measurement device includes a first port configured to receive a test strip and a second port configured to connect with a power source or a computer via a cable. An analyte disposed on the test strip is analyzed via the strip port and data is uploaded/downloaded via the second port or the internal battery can be charged through the second port. In this example, a shutter is connected to or integrated with the device and configured to move at least between a first position and a second position. In the first position, the first port is physically covered and in the second position, the second port is physically covered. In other words, the shutter can provide a physical barrier to at least one of the ports while the other port is used. In a certain embodiment, the shutter may also be placed in a position such that access to both ports is simultaneously barred by the shutter.

In other embodiments, the apparatus for preventing shock from a measurement device includes a cable configured to connect the measurement device with a computer or a power source to recharge the internal battery. A connector on an end of the cable is configured to interface with a computer port of the measurement device. The device also includes a barrier disposed around the connector. The barrier may define a cavity with a perimeter that substantially matches a corresponding perimeter or outline of the measurement device. When connected with the measurement device, an end of the measurement device occupies the cavity when the connector is inserted into the port. Also, the barrier prevents access to a strip port of the device when the connector is inserted into the computer port.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE EMBODIMENTS OF THE INVENTION

Measurement devices are often used to provide analysis of various types of analytes. Self monitoring blood glucose (SMBG) and continuous glucose monitoring (CGM) devices, for example, are examples of measurement devices that are often employed to measure the blood glucose level of a user from a small sample of blood. The information obtained from the analysis of the user's blood sample or from a history of blood glucose measurements can be used to diagnose, treat, or control diseases such as diabetes. Tracking the blood glucose level of a user over time, for example, can provide insight into the progression of diabetes, the effectiveness of the treatment received, and the like. Changes in the results of the analysis performed by the measurement device can allow the user's treatment to be altered accordingly.

To make this process easier, many measurement devices have the ability to interface with a computer such that the results of the analysis can be automatically recorded and stored on the computer. In addition to utilizing a port to interface with a computer to record and store results, the port can be used to recharge the internal battery of the device.

In order to perform these functions, the measurement device often has circuitry that is used to perform the analysis of the analyte, circuitry to interface with the computer to upload the results of the analysis, and circuitry to recharge the internal battery. Embodiments of the invention relate to systems and methods for preventing a user from being electrically shocked while these functions, among others, are performed. More specifically, embodiments of the invention relate to systems and methods including physical barriers that cover or block access to electrical interfaces to prevent a user from electrical shock while using the measurement device. The physical barrier may be movable such that certain interfaces can be exposed for use while other interfaces are covered to prevent or minimize, among other things, electrical shock.

Embodiments of the invention include shutters that act as physical barriers to the ports of the device. For example, the shutter may block access to one port while allowing access to another port. The shutter can also be configured to block access to more than one port at a time, such as, for example, when the device is not being used to measure blood glucose level or connected to another device. A shutter that is configured to cover more than one port in a particular position has the additional benefit of protecting both ports from environmental factors including, but not limited to, dust and water at the same time. In this configuration, the shutter can be moved to uncover a particular port while the other port remains covered.

In addition, the strips or connectors can be configured to interface with a given port in a manner that blocks access to one port while accessing another port. For example, the plug of a connector may be configured to physically block access to one port while electrically interfacing with another port. In another embodiment, the device may include a single port that is mechanically and/or electrically configured to interface with both a test strip and a power connector or computer cable.

The risk of electrical shock, as indicated above, partially stems from the external accessibility of the device's electrical interfaces. A measurement device may include, for instance, a port for receiving test strips and a port for connecting or linking to a computer or receiving power form an external power source. These electrical interfaces are often exposed to the environment and are often in contact with a user. To prevent electrical shock or minimize the risk of electrical shock, the measurement device may include a physical barrier configured to prevent physical contact with at least one of the ports while another port is in use. A physical barrier prevents contact with the port, thereby ensuring that the physically isolated port is not a source or part of the conduction path of an electrical shock.

Embodiments of the invention may include a shutter arrangement that provides a physical barrier. Because a measurement device may be manufactured using a wide variety of different form factors, the shutter arrangement disclosed herein can take various forms and can be adapted to the form factor of the specific device and the locations of the electrical interfaces. One of skill in the art, with the benefit of the present disclosure, can appreciate the applicability of the invention to various form factors of measurement devices.

Embodiments of the shutter arrangement or physical barrier can be integrated with the measurement device and can be manually and/or automatically operated. In some embodiments, the physical barrier can be integrated into a separate device, such as the cable that connects the measurement device with the computer or exterior power source. In general, however, the physical barrier may be configured to physically prevent access to at least one electrical interface. Alternatively, the physical barrier may enable access or physical contact to only one electrical interface at a time. Advantageously, the shutter arrangement or physical barrier is more effective than conventional software solutions, which still have a risk of electrical shock because the user may only be given a visual warning of a potential electrical shock.

As described herein, the physical barrier may prevent simultaneous access to multiple electrical interfaces. By providing a physical barrier, electrical shock can be eliminated. Alternatively, the risk of electrical shock can be reduced by physically barring access to at least one electrical interface. The barrier can also be configured to block access to all ports in a default position until it is moved to allow access to one (and only one) port for immediate use in one embodiment.

Figure 1A:
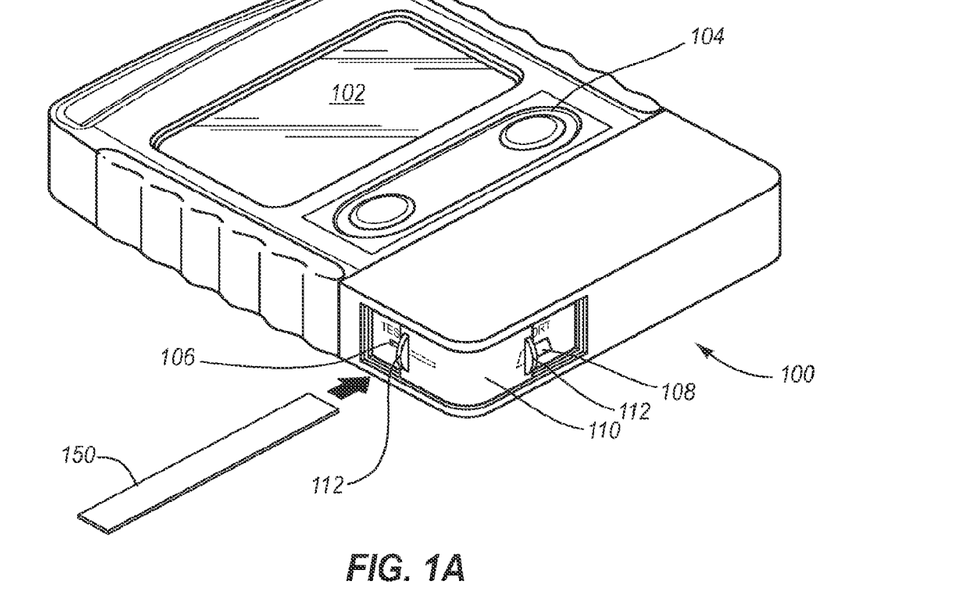
FIG. 1A illustrates a perspective view of a measurement device and a physical barrier that reduces the risk of electrical shock from the device by preventing simultaneous access to the ports or electrical interfaces of the measurement device.

FIG. 1A illustrates an embodiment of a measuring device 100. The measuring device 100 may include a display 102 and a user interface 104. The display 102 may be used to display results of an analysis of an analyte performed by the device 100. For instance, the measurement device 100 may be a blood glucose meter that measures the blood glucose level from a blood sample. The blood glucose level is then displayed on the display 102. The measured blood glucose level can be stored on the device for upload to a computer at a later time.

The device 100 may include one or more electrical interfaces. A port 106, is one example of an electrical interface. The port 106 may be configured to receive a test strip 150 and electrically connect with the test strip 150. Typically, the test strip 150 is inserted into the port 106 and then loaded with an adequate blood sample. Once the test strip 150 is properly inserted in the port 106 and a blood sample is properly transferred to the test strip 150, the device 100 measures the blood glucose level in the blood sample and displays the result on the display 102.

The device 100 may also include a second electrical interface, which is illustrated as a computer port 108 in FIG. 1A. The port 108 can be used to connect the device 100 to a computer or to a power source. In some instances, the computer also serves as the power source for the device and also provides the energy needed to recharge the power source of the device 100. Because both the port 106 and the port 108 are located on the outside of the device 100 or are externally accessible to a user, the circuitry associated with the ports 106 and 108 can come into contact with the environment including the user as previously stated. This type of contact, in certain instances, can result in an electrical shock to the user and may have other consequences such as device failure or data corruption.

FIG. 1A further illustrates a shutter 110, which is one example of a physical barrier. The shutter 110 is configured to physically prevent or block at least one of the electrical interfaces (e.g., the port 106 and/or the port 108) from contact with the environment, including the user. The shutter 110 may ensure that only one of the ports 106 and 108 can be used at a time. The shutter 110 provides a physical barrier to one of the ports while the other port is available for use. For instance, the port 106 may be covered or blocked by the shutter 110, or a portion thereof, while the port 108 is accessible. Alternatively, the port 106 may be available when the port 108 is covered or blocked by the shutter 110 or by at least a portion of the shutter 110. The shutter 110 may not completely cover the port 106, but may still prevent electrical contact with the port 106.

FIG. 1A illustrates that the shutter 110 may be flexible and able to adapt to device configurations that place ports on different sides or surfaces of the device 100. The shutter 110 may be formed of an insulating or non-conducting material such that it does not interfere with the electrical function of the port 106 or the port 108. By way of example only, the shutter 110 may be formed of polyethylene or polypropylene or any other plastic or suitable material.

Figure 1B:
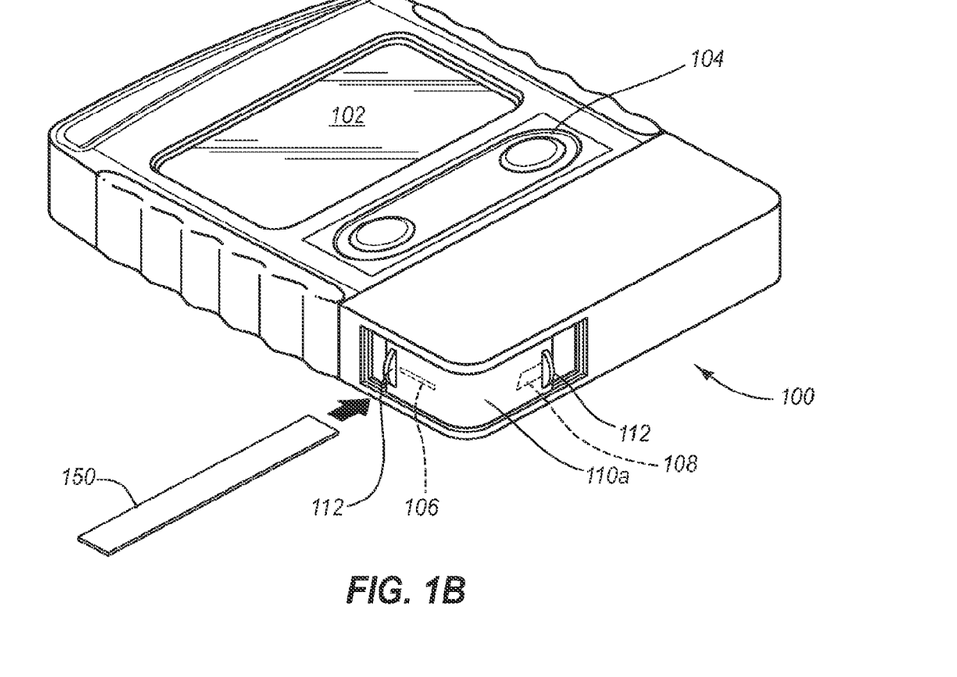
FIG. 1B illustrates a perspective view of a measurement device with a physical barrier that covers both ports at the same time.

FIG. 1B is similar to FIG. 1A, but illustrates another example of a shutter 110a. In this example, the shutter 110a is configured such that is able to cover both the port 106 and the port 108 at the same time. Sliding the shutter 110a in one direction or another can expose a particular port while the other port remains covered. In a certain embodiment, the shutter 110a is biased such that both ports 106 and 108 are covered by default. After a user performs an analysis using the port 106 or connects the device 100 to a computer using the port 108, the shutter 110a returns to the default position illustrated in FIG. 1B automatically because of the bias. The shutter 110a illustrated in FIG. 1B can protect both ports 106 and 108 from ingress of water, dirt, or other contaminants when the device 100 is not is use by covering both of the ports 106 and 108.

Figure 2:
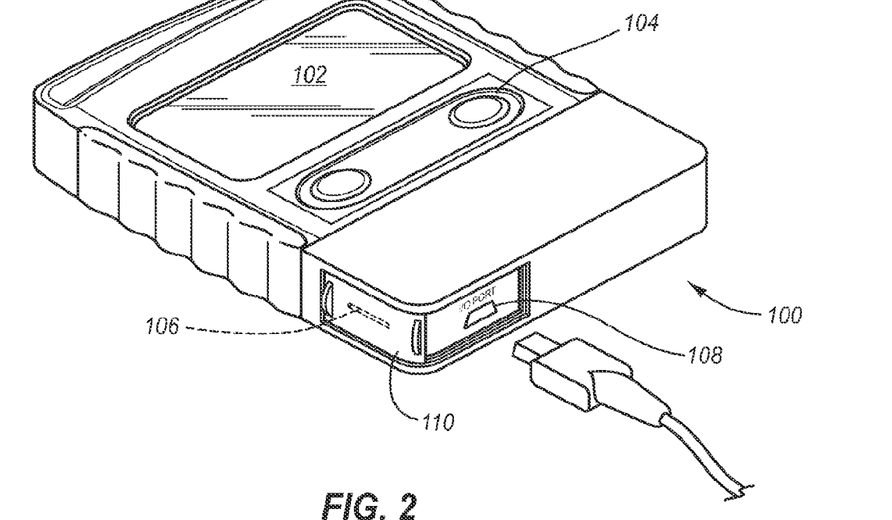
FIG. 2 illustrates a perspective view of a measurement device with a shutter whose position can be arranged to provide a physical barrier to an electrical interface of the device while allowing access to another electrical interface of the measurement device.

FIG. 2 illustrates another illustration of the measurement device 100 with a shutter 110 or a shutter 110a. In this example, the shutter 110 is in a first position covering the port 106 while the port 108 is uncovered. When the shutter 110 is in this position, the measurement device may be connected to another device such as a computer or power source via the port 108 (e.g., a USB port), which remains accessible while the port 106 is covered or blocked. While connected to the computer, for instance, in this manner via the port 108, the device can upload/download information or other data such as firmware or analysis data, charge the rechargeable batteries, and the like. The shutter 110 prevents a user from using the measurement device 100 to perform a blood glucose level measurement while the port 108 is in use and prevents the user from being electrically shocked by physically barring access to the port 106.

Figure 3:
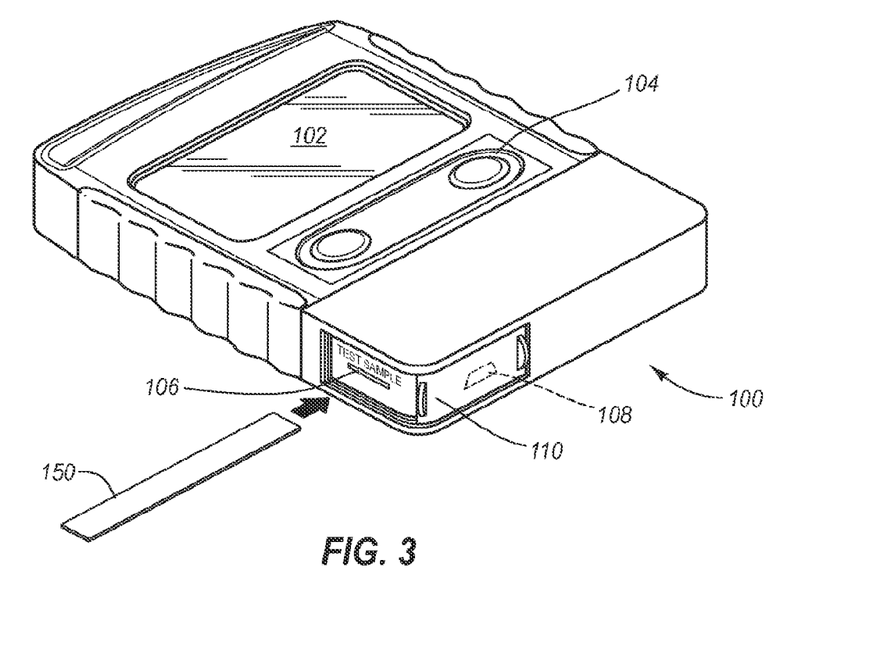
FIG. 3 illustrates another view of a measurement device with a shutter whose position can be arranged to enable access to only one electrical interface of the measurement device at a time.

FIG. 3 illustrates the shutter 110 in a second position. In this example, at least a portion of the shutter 110 is covering the port 108 while the port 106 is uncovered or accessible. In this position, the measurement device 100 may be used to measure blood glucose levels while the shutter 110 physically prevents the measuring device 100 from being connected to a computer or other device via the port 108.

As previously mentioned, the location and configuration of the shutter 110 may depend on the form factor of the device 100. Thus, the shutter 110 can be located on or be configured to adapt to one or more surfaces or sides of the device 100. In this example, the shutter 110 is located on the side surface of the device 100. When the shutter 110 moves from covering the port 108 to covering the port 106, the shutter 110 adapts according to the form factor of the device 100. In FIGS. 2 and 3, the shutter 110 moves from a first side of the device to a second side of the device. The device 100 may have a track or other guiding structure that directs the shutter 110 from one position to another position.

Advantageously, the corner of the device 100 can aid in retaining the shutter 110 in either the first or second position as some force may be needed to slide the shutter 110 from one position to another position. In addition, the operation of the shutter 110 can be manual, automatic, or partially automatic. For example, a user may manually move the shutter 110 from the first position to the second position. In another embodiment, the insertion of a cable into the port 108 may cause the shutter 110 to automatically move to cover or block the port 106

Figure 4:
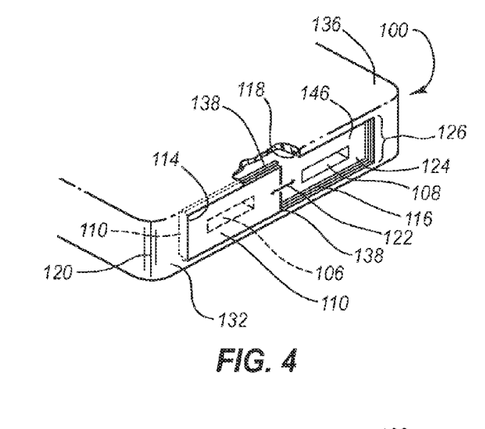
FIG. 4 is a perspective view of one embodiment of a shutter arrangement that provides a physical barrier to an electrical interface of a measurement device.

FIG. 4 illustrates one embodiment of a shutter arrangement that includes a physical barrier such as the shutter 110. In this illustration, the device 100 has an end with electrical interfaces represented by the ports 106 and 108. In this example, the ports 106 and 108 are on the same side of the device 100. The port 106 may be configured to receive test strips while the port 108 may be configured to interface with another device such as a computer or a power source via a cable.

In FIG. 4, the shutter 110 is covering or physically barring the port 106 (shown in dotted lines) while the port 108 is exposed and accessible for use. The shutter 110 may physically prevent a user from contacting the port 106 by blocking the port. Sliding the shutter 110 in the directions of arrow 122 allows one of the ports 106 and 108 to be covered while the other is exposed or accessible for use. As a result, the position of the shutter 110 can impact the use of the device 100.

In FIG. 4, shutter arrangement of the device 100 is configured with an enclosure 124. The shutter 110 may be disposed within the enclosure 124 such that the shutter 110 becomes an integral part of the device 110. In one embodiment, the shutter 110 may by intended to remain inside the enclosure 124. To keep the shutter 110 inside the enclosure 124, rails 116 and 118 have been formed into an end of a case or housing of the device 110. The rails 116 and 118 may alternatively form a track that cooperates with an engagement portion 138 of the shutter 110. In one embodiment, the engagement portion 138 fits within the track such that the shutter 110 can slide in the directions indicated by the arrow 122. The track formed by the rails 116 and 118 guides the shutter 110 as the shutter 110 slides from a position where the port 106 is covered to a position where the port 108 is covered. As previously indicated, the shutter 110 may be placed in a position where both the ports 106 and 108 are covered.

The rails 116 and 118 may be a single rail system or a dual rail system. In a single rail system, the shutter 110 is held within the enclosure 124 between the rails 116, 118 and the surface 146 of the device 100. The track in this example is formed by the surface 146 and the rails 116 and 118. In this example, the surface may be used, via friction, to hold the shutter in any particular position. In a certain embodiment, an end the enclosure 124 may be configured to form an interference fit with the shutter 110 when the shutter 110 is in specific positions. For example, an interference fit may be used to keep the shutter 110 in a default position.

In one example of a dual rail system, the engagement portion 138 of the shutter 110 is held by the rails 116 and 118. In other words, a portion of the rail 116 and 118 is between the shutter 110 and the surface 146. In this example, a dual rail system may hold the shutter 110 is a particular position relative to the ports 106 and 108. In this example, the rails 116 and 118 can hold the shutter 110 a short distance away from the surface 146 such that the ports 106 and 108 do not interfere or inhibit movement of the shutter 110 between the various positions as it slides within the enclosure 124.

The housing or case 136 of the device 100 may be molded plastic, metal, or other suitable material or any combination thereof. The mold or machinery used for form the case 136 may be set to create the enclosure 124 and may be formed, by way of example only, in two halves that are joined during manufacture. The shutter 110 may be placed in the enclosure 124 before the two halves of the case are connected together. Alternatively, the shutter 110 may have sufficient flexibility to permit the shutter 110 to be installed in the enclosure 124 after the case 136 is formed.

In this example, the end of the case 136 extends out laterally from the top and bottom surfaces to form the enclosure 124. In one embodiment, the enclosure 124 may not occupy an entire end of the device 100. In this example, the surface 132 is formed such that the surface 132 smoothly transitions to the outer surfaces of the rails 116 and 118. In one example, the exterior surface 132 of the end of the device 100 includes the rails 116 and 118.

The enclosure 124 may be formed by the surface 120 and the rails 116 and 118. The enclosure 124 is then bounded by the surface 146 that is inset relative to the surface 132. The rails 116 and 118 may have a height that is sufficient to retain the shutter 110 inside the enclosure 124 or inside the track formed by the rails 116 and 118 while permitting access to the shutter 110 through the opening 126. The opening 126 between the rails 116 and 118 is sufficient to allow a user to slide the shutter 110 back and forth with a finger, for example. The opening 126 is also sized and configured to allow the test strips to be inserted into the port 106 and to allow a cable to be inserted into the port 108 easily. The opening 126 has dimensions that allow the test strips and/or cable connector to be inserted into the corresponding interfaces. Optionally, the shutter 110 may have a handle (e.g., the handle 112 shown in FIG. 1A) that allows the user to move the shutter 110 more easily from a first position to a second position or to any other position within the enclosure 124.

In addition, the enclosure 124 and shutter 110 may have a configuration to ensure that one of the ports remains covered during use or to insure that access to at least one port is barred or to prevent electrical contact with the covered port. For instance, the insertion of a cable into the port 108 may constrict the lateral movement of the shutter 110 within the enclosure 124 such that the port 106 remains covered. In other words, the cable may act as a stop that prevents or limits lateral movement of the shutter 110 such that the port 106 remains covered or blocked as long as the cable is connected with the port 108. Similarly, a test strip 150 inserted into the strip port 106 may also act as a stop to prevent the port 108 from being uncovered.

Alternatively, the shutter 110 may have a friction fit inside the enclosure 124 that holds the shutter in a particular position yet allows a user to move the shutter 110 as needed from one position to another position. For example, the end portions 114 of the enclosure 124 may be narrower than a thickness of the shutter 110 or have about the same thickness of the shutter 110. As the shutter 110 is moved into a particular position, the friction between the end portion of the enclosure 124 and the shutter 110 may hold the shutter in a particular position. The shutter 110 thus forms a physical barrier that permits access to only one of the ports 106 and 108 at a time and prevents electrical shock.

The orientation of the shutter 110 or other physical barrier can vary according to the placement of the ports 106 and 108 on a given device 100. As a result, the shutter 110 may move side-to-side or up-and-down relative to the ports. As previously mentioned, the shutter 110 may move from one side or surface of the device to another side or surface of the device. The structure of the enclosure 124 can be adapted such that the shutter 110 can be moved to cover or electrically block at least one port. In situations where the ports are not on the same side of the device or not in the same surface planes (e.g., as illustrated in FIG. 1A), the shutter 110 may have a flexibility to accommodate the relative positions of the ports 106 and 108. In addition, the enclosure 124 may be shaped to accommodate the various surface planes. FIG. 1A, for example, illustrates that the shutter 110 is able to deform to bend around a corner of the device 100 in order to accommodate ports that are in different surface planes or sides of the device 100.

Figure 5:
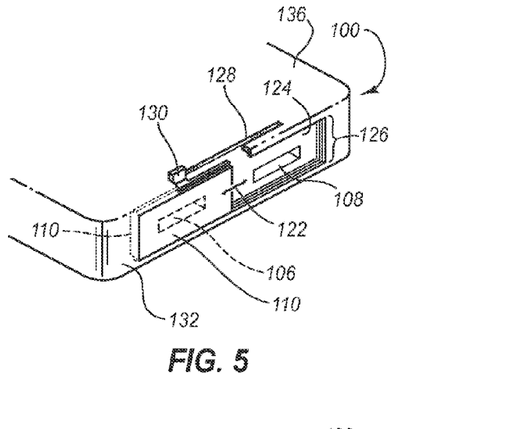
FIG. 5 illustrates another embodiment of a shutter arrangement that provides a physical barrier to an electrical interface of a measurement device.

In a certain embodiment illustrated in FIG. 5, the shutter 110 may include a tab 130 extending laterally from a body of the shutter 110. The tab 130 may be positioned to extend out of a slot 128 that is formed in the case 136 of the device 100. In this example, the enclosure 124 encases the shutter 110, but the tab 130 may be used to slide the shutter 110 from one position to another position. The opening 126 in FIG. 5 may be limited in size to openings that are sufficient to provide access to the ports 106 and 108. The surface 132 on the end of the device 100 provides access to the ports 106 and 108 through the opening 126. The ports 106 and 108 are inset from the exterior surface 132 of the device 100 such that the shutter 110 has clearance to slide between at least two positions and prevent access to at least one of the ports 106 and 108. In this example, the rails that define a portion of the enclosure 124 may be shaped to permit access to the ports 106 and 108.

Figure 6A:
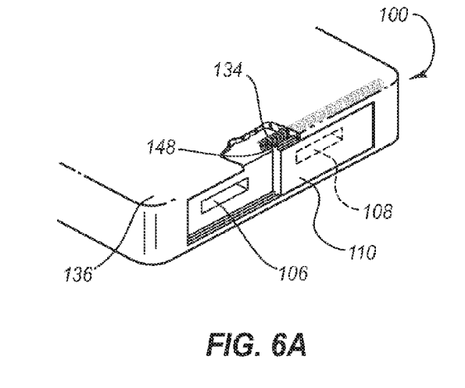
FIGS. 6A and 6B illustrates a certain embodiment of a shutter arrangement that includes a mechanical bias to maintain the shutter in a default position.
Figure 6B:
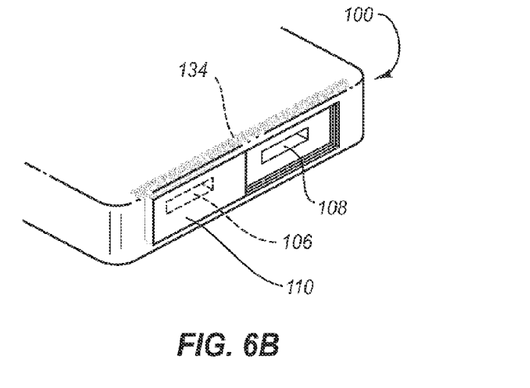

FIGS. 6A and 6B illustrates another embodiment of the shutter 110. In this example, the device includes a bias mechanism 134 that biases the shutter 110 in a particular or default position. In this example, the bias mechanism 134, such as a small spring, causes the strip port 106 to be available for use by default by pulling against the bias engagement 148. The bias mechanism 134 is located inside the enclosure 124 in this example. The bias mechanism 134 may be placed between the shutter 110 and a wall of the case 136. The case 136 may have structure to accommodate the bias mechanism 134 and the expansion or contraction of the bias mechanism 134. Thus, the bias mechanism 134 can be above the shutter 110 or by the side of the shutter 110 or in another location.

Movement of the shutter 110 to cover the port 106, as illustrated in FIG. 6A, extends the bias mechanism 134. The force exerted by the extended bias mechanism 134 returns the shutter 110 to the default position when the shutter is released. When the device is connected to a computer via cable, the shutter may be moved against the bias mechanism 134 to allow insertion of the cable. Once the shutter is then released, the bias mechanism 134 attempts to push or pull the shutter 110 back to a default position. Once the cable is inserted into the port 108, the cable may act as a stop to ensure that the port 106 remains covered and prevent the shutter 110 from returning to the default position. In this example, the bias mechanism 134 automatically uncovers the port 106 and covers the port 108 when the cable is removed. This advantageously leaves the port used for test strips to be open and accessible by default.

One of skill in the art, with the benefit of the present disclosure, can appreciate that the bias mechanism 134 can be configured in different arrangements to keep shutter 110 is a default position. For example, the shutter 110 and ports 106 and 108 can be designed so that the shutter 110 would cover both of the ports 106 and 108 in its resting or default position. The shutter 110 can be moved to allow access to either 106 or 108 (but not both) at the desired time. This arrangement could offer a higher degree of protection against dust and moisture ingress as both ports would be covered unless actively in use.

Figure 7:
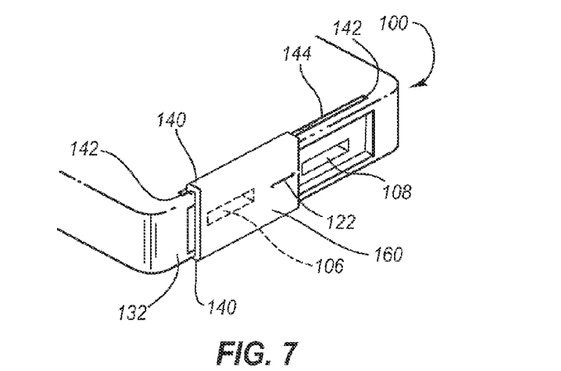
FIG. 7 illustrates a certain embodiment of a shutter that controls access to electrical interfaces of a device.

FIG. 7 illustrates another embodiment of a physical barrier, which is illustrated as a shutter 160. In FIG. 7, the shutter 160 may be configured to connect to the external surface of the device 100 or to the end of the device 100. In this example, the shutter 160 has curved ends or formed ends that cooperate with a groove 144 formed in the case of the device 100. The shutter 160 can have sufficient stiffness such that the shutter 160 is difficult to remove from the end of the device 100, but is formed to facilitate movement relative to the groove 144. The shutter 110 can slide along the groove 144 (formed on opposite sides of the device in one embodiment) to selectively cover or block access to one of the ports 106 and 108. The groove 144 typically does not extend all the way across the device 100 to prevent the shutter 110 from disengaging from the device 100. Thus, the ends of the groove 144 acts as a stop to constrain movement of the shutter 160 relative to the ports 106 and 108. When a cable is inserted in the port 108, for instance, the end of the groove 144 and the cable can retain the shutter 160 in a position to prevent access to the port 106.

The shutter 160 also includes clamps 140 that hold the shutter 160 on the end of the device 100. The clamps 140 may be shaped to follow the contours or outline of the device 100. The clamps 140 may come into contact with the device 100. Thus, the clamps 140 may be curved for a curved device form factor, square for a square device form factor, and the like. This allows the shutter 160 to have a small footprint while resting flush against the external surface of the device and be able to slide along the surface 132 of the device 100. When a cable is inserted into the port 108, the cable may act as a stop to prevent the port 106 from being uncovered. A stop 142 (e.g., the end of the groove) may be formed on both sides of the device 100 to retain the shutter 160 inside the grooves 144. As a result, the stop 144 and the cable may restrict lateral movement of the shutter 110 when access to port 106 is required. Similarly, a test strip and the stop 142 may also act to restrict lateral movement of the shutter when access to port 108 is needed. At the same time, the shutter 160 prevents physical access or contact to the port not in use. Although the ports 108 and 106 are illustrated as being inset from the surface 132 of the device 100, one of skill in the art can appreciate that the port 106 and 108 may be flush with the surface 132 of the device 100.

Figure 8:
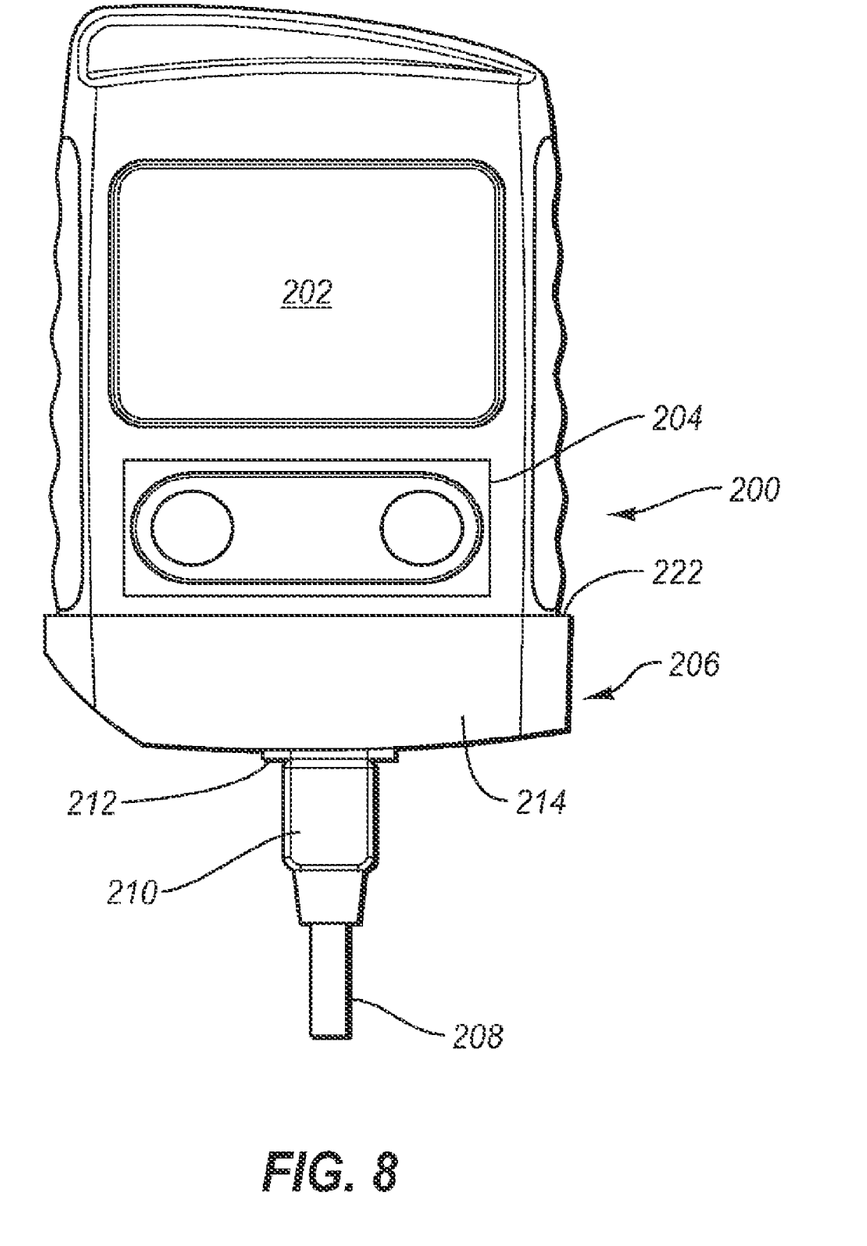
FIG. 8 is a perspective view of a physical barrier that is integrated with a cable that is connected with a port of a measurement device.
Figure 9A:
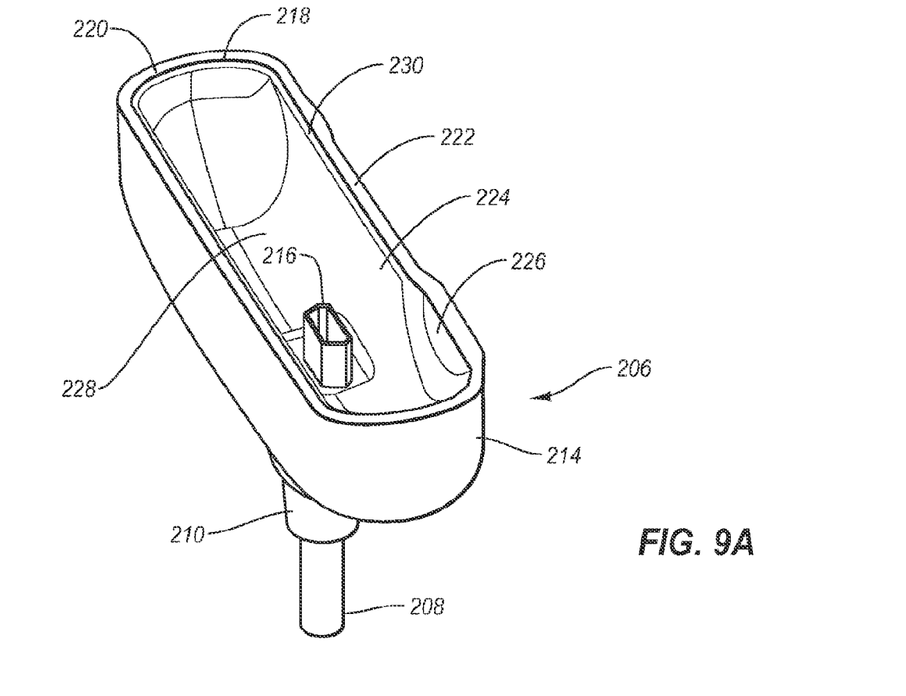
FIG. 9A illustrates a perspective view of a physical barrier integrated with a cable that is not connected with a port of a measurement device.
Figure 9B:
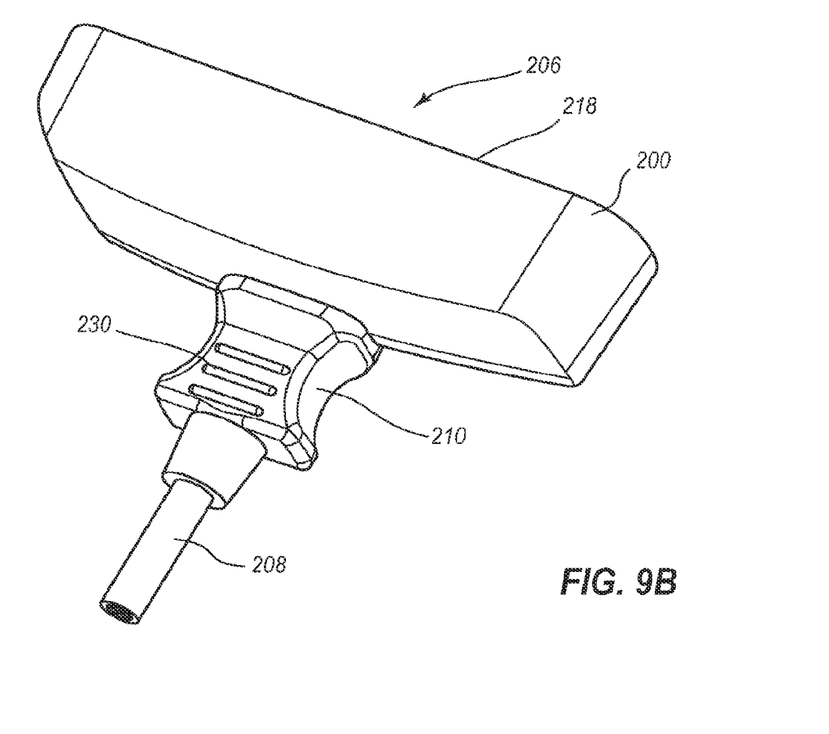
FIG. 9B illustrates another perspective view of a physical barrier integrated with a cable.

FIGS. 8, 9A and 9B illustrate another embodiment of a physical barrier 206 to prevent electrical shock from a measurement device or while using a measurement device. FIG. 8 illustrates the physical barrier when connected to a device and FIGS. 9A-9B illustrates the physical barrier when disconnected from the device. The measurement device 200 illustrated in FIG. 8 may include a display 202 and a user interface 204. One of skill in the art can appreciate that the form factor of the measurement device and capabilities of the measurement device can vary and that the physical barrier described herein can be adapted to those form factors.

In FIGS. 8, 9A and 9B, the physical barrier 206 can be an integral part of the cable 208 and permanently connected to the cable 208. Permanently connecting the physical barrier 206 with the cable 208 insures that the physical barrier is used with the device and thus prevents electrical shock. The cable 208 includes a barrier 206 that is connected on a grip 210 of the cable 208. In one embodiment, the barrier 206 is permanently connected to the end of the cable 208. The barrier 206 and the grip 210, for example, may be integrally molded or fixed with thermal bonding, adhesives, and the like. The barrier 206 includes a body 214 that may be molded or formed to have a particular shape that allows the barrier 206 to prevent access to at least one port and, in some embodiments, provide stability to the connection between the cable 208 and the device 200. The cable 208 passes through the physical barrier 206 at insertion point 212. When the cable 208 is connected with the device 200, as shown in FIG. 8, the barrier 206 is configured to prevent access to other ports including the strip port while the connector on the end of the cable 208 is connected to the computer port of the device 200. More specifically, the barrier 206 in this example completely encompasses an end of the device 200 including any other ports. As a result, access to the other ports is barred.

The barrier 206 can take a plurality of different configuration that are adapted to the form factor of the device 200. In general, the physical barrier may include a port cover that covers at least the strip port when the connector 216 is inserted into a corresponding port on the device 200. In this example, the body 214 forms a cradle or shroud that covers an end portion of the device 200, including the strip port and other ports of the device 200, when the connector 216 is inserted into a corresponding port on the device 200, as shown in FIG. 8. The body 214 is typically configured such that at least a portion of the body 214 covers the strip port. As a result, a strip port that is on a different side of the device than the computer port is still physically covered by the barrier 206 when connected.

The physical barrier to the strip port may be achieved by forming the body 214 to conform with the form factor of the device 200. In this example and as illustrated in FIG. 9A, the barrier 206 includes a perimeter 222 that corresponds to a perimeter of the device 200 and permits the device 200 to be inserted into the cavity 228 of the body 214. The perimeter 222 is typically larger than the perimeter of the device 200 to permit the device to fit within the cavity 228. The body 214 may have indentations 226 or other configurations to conform with the form factor of the device 200. In another embodiment, the body 214 may include an engagement structure 230 that allows the barrier 206 to engage a corresponding structure on the device 200 and securely hold the barrier 206 in a connected position. By way of example, the engagement structure 230 may be a clip that provides sufficient force to connect the barrier 206 with the end of the device 200. The engagement structure 230 can provide additional mechanical connection and stability when the barrier 206 is connected with the device 200.

FIG. 9B illustrates another perspective view of the barrier 206. FIG. 9B illustrates that the body 214 of the barrier 206 is formed to cooperate with an end of the device 200. In this example, the grip 210 of the cable 208 may include ridges 230, which can facilitate the insertion and removal of the barrier 206 with respect to a device 200. The grip 210 in this example is configured to provide a visual indicator to a user of where to grip the barrier 206 when inserting or removing the barrier 206. In addition, the grip 210 may have a shape that is configured to help a user grasp the barrier 206 during insertion or removal of the barrier 206 relative to a measuring device.

Figure 10:
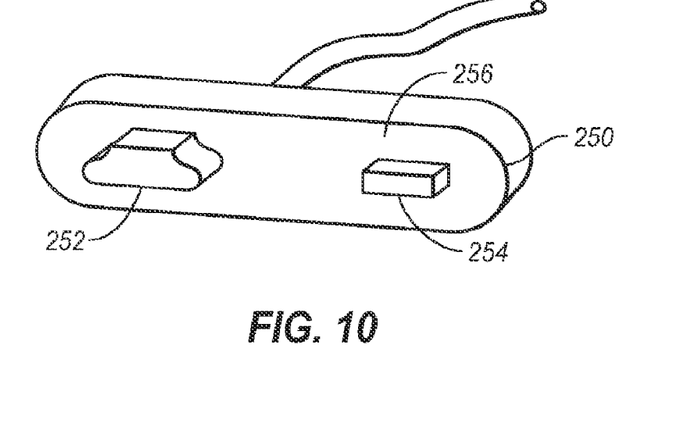
FIG. 10 illustrates another embodiment of a physical barrier to prevent access to an electrical interface of a measurement device while another electrical interface is in use.

FIG. 10 illustrates another embodiment of the barrier 250. In this example, the connector 252 extends through the barrier 250, with the cable extending from the other side of the barrier 250. The barrier 250 also includes a plug 254 located such that the plug 254 interfaces with a strip port of a device when the connector 252 is inserted in a computer port of the same device. In this manner, the plug 24 and/or a portion of a body 256 of the barrier 250 prevents access to the strip port of the device. The plug 254 may be sufficient to block the strip port or may provide an alignment feature to properly connect the barrier 250 with a device.

Figure 11:
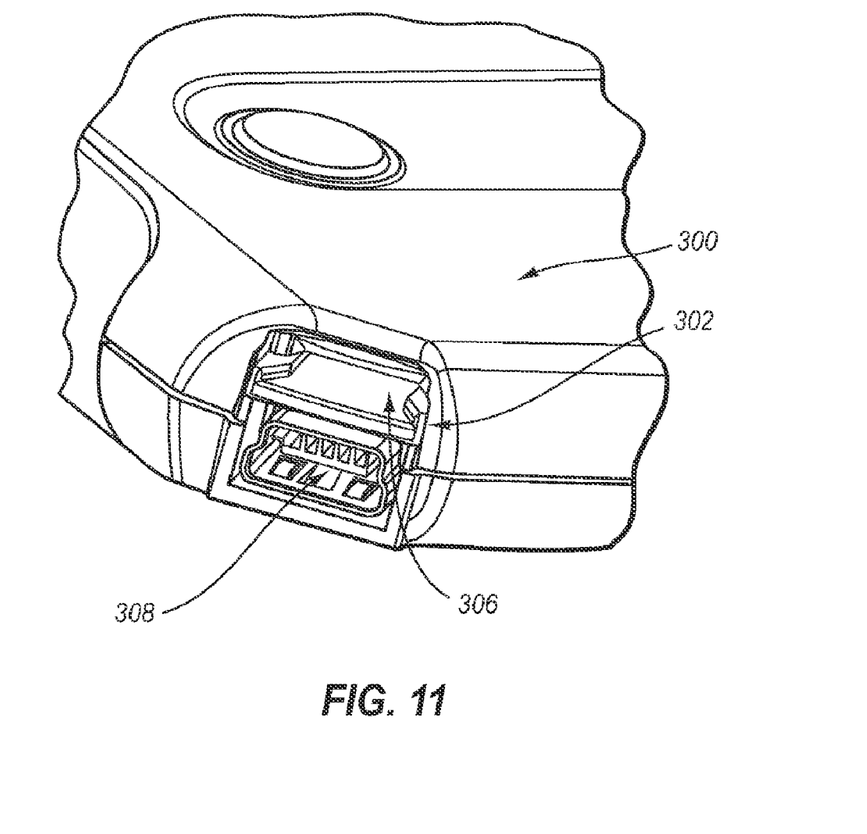
FIG. 11 illustrates an embodiment of an electrical interface that includes both a test strip port and a computer or recharge port.

FIG. 11 illustrates one embodiment of a measurement device 300 with a unified interface 302. The interface 302, in this example, provides access to both the port 306 and the port 308. In one embodiment, the interface 302 includes a single electrical interface that is configured to receive both a test strip 150 and a computer or power connector. The physical arrangement of this interface 302 of port 306 relative to the port 308 prevents a user from using the device, for example, to both perform a glucose test measurement and connect to a computer or power source. In one embodiment, the close proximity of the port 306 and the port 308 prevents both ports from being used simultaneously.

Figure 12A:
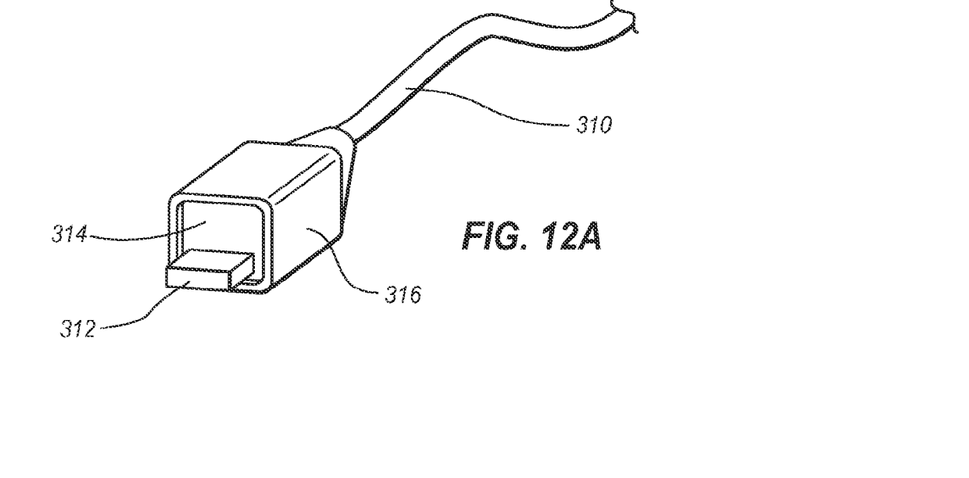
FIG. 12A illustrates one embodiment of a cable that provides a physical barrier to at least one of the ports while another port is used.

When the interface 302 includes both the port 306 and the port 308, the cable 310 illustrated in FIG. 12A can provide a physical barrier to prevent electrical shock. In FIG. 12A, the cable includes a connector 312 that is configured to connect with the port 308. The cable 310 also includes shroud 316 with a raised barrier portion 314 that is configured to cover the port 306 when the cable 310 is connected with the device 300 and the connector 312 is inserted into port 308. The barrier portion 314 extends up from the connector 312 a sufficient height to cover the port 306 when connected. The unified interface 302 has an opening that can receive the cable 310 and cooperate with the barrier portion 314 to bar access to the port 306 during user of the port 308

Figure 12B:
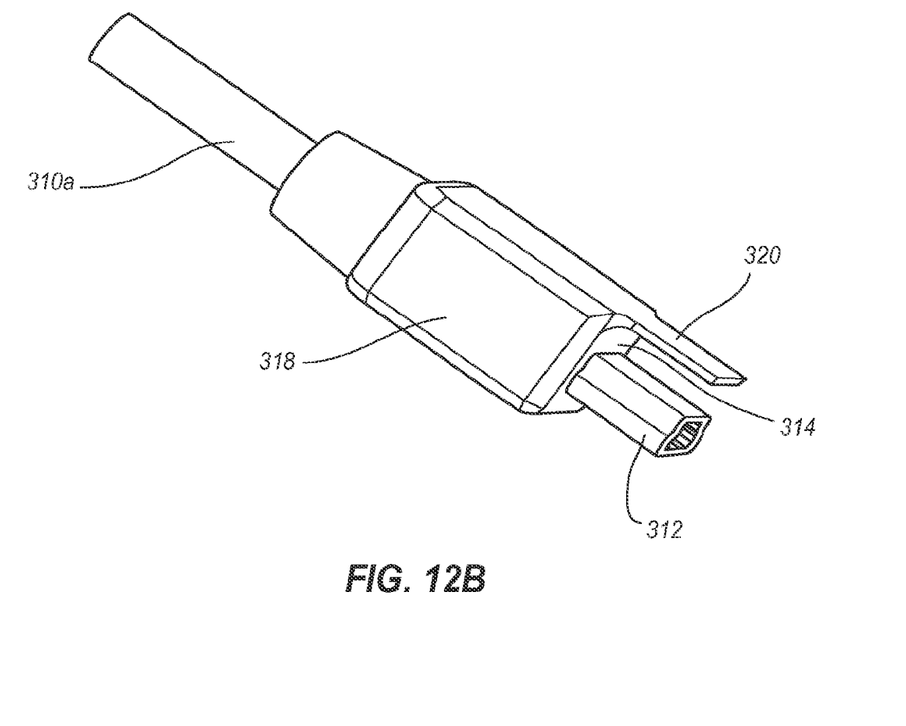
FIG. 12B illustrates one embodiment of a cable with a plug that provides a physical barrier to a port on a measurement device.
Figure 12C:
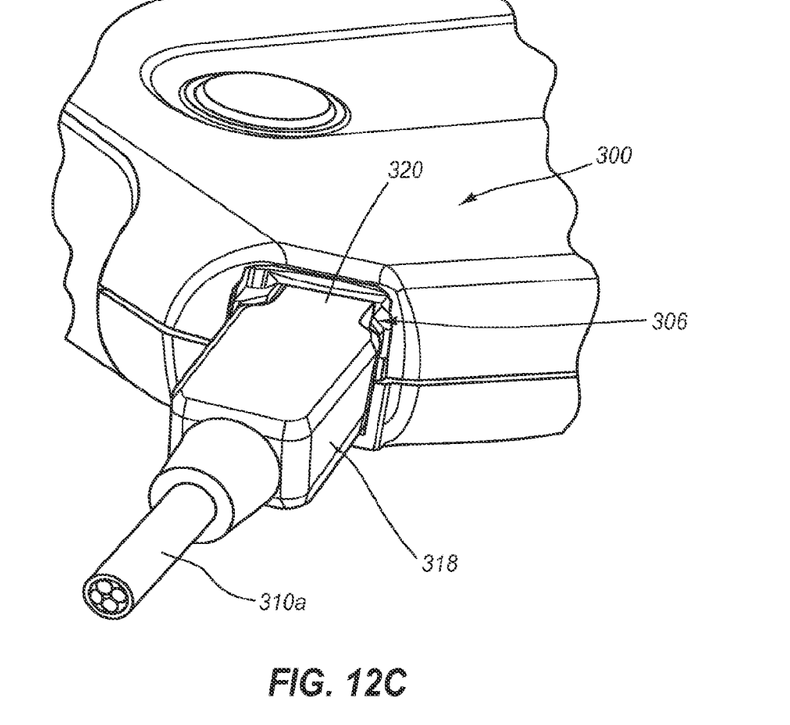
FIG. 12C illustrates the cable of FIG. 12B connected with a measurement device.

FIG. 12B illustrates an embodiment of a cable 310a with a shroud 318 that includes a connector 312 and a plug 320 that extends out from the barrier portion 314. In this example, the plug 320 is configured to be inserted into the port 306 when the connector 312 is inserted into the port 308. The plug 320 is typically non-conductive, and prevents a strip from being inserted into the port 306. FIG. 12C illustrates the cable 310a when connected with the device 300. As shown, the plug 320 extending laterally from the shroud 318 is inserted into the port 306 when the connector 312 of the cable 310a is connected to the device 300.

Figure 12D:
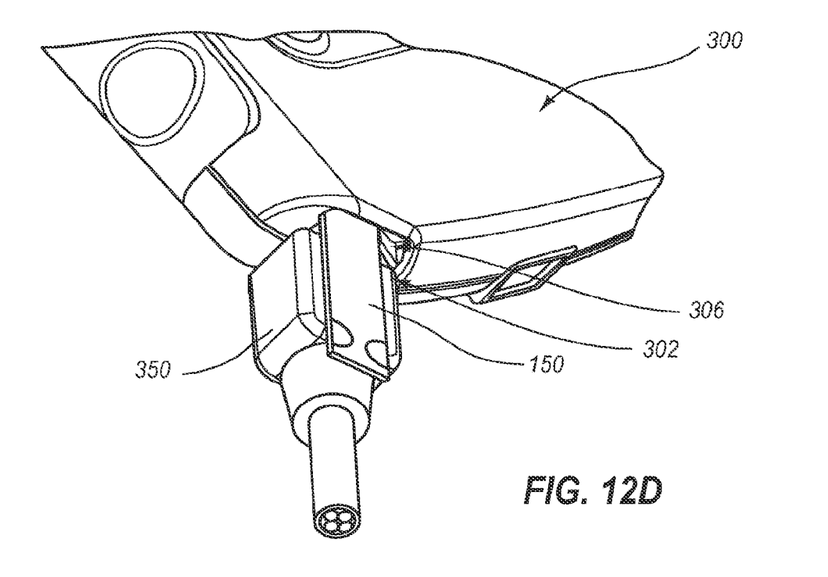
FIG. 12D illustrates ports that are configured such that access to one port is hindered when using conventional connectors.

FIG. 12D illustrates an example of a conventional cable 350 that is inserted into a port 308. In this example, however, the ports 306 and 308 of the interface 302 are configured such that the insertion of the cable 350 hinders or blocks access to the port 306. A user is unable to access the port 306 because of the proximity or relative positioning of the ports 306 and 308. Hindering access, in this example, can prevent a user from using both ports at the same time and thereby prevent electrical shock.

Figure 13:
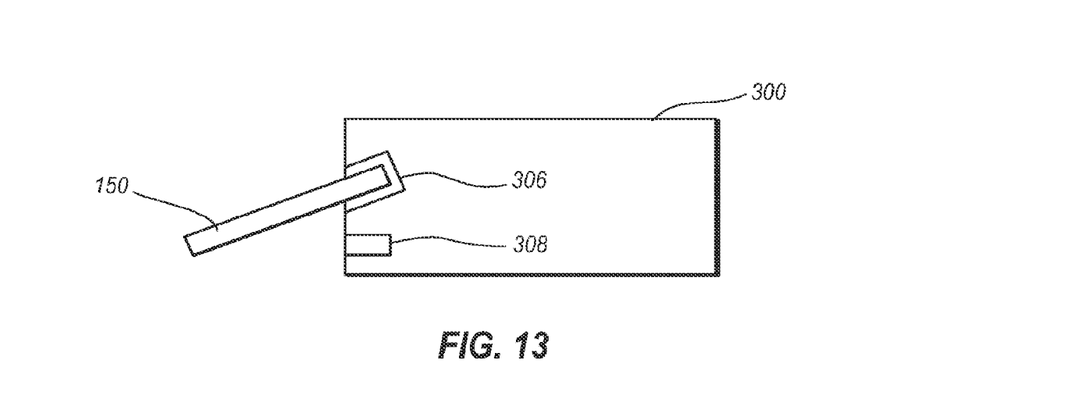
FIG. 13 illustrates another embodiment ports in a measurement device that are arranged to facilitate bar access to one port while another port is in use.

FIG. 13 illustrates an example of inserting a test strip 150 into the interface 302 of the device 300. In this example, the port 306 is angled with respect to the port 308. Because the port 306 is angled, the test strip 150 at least partially covers the port 308. The test strip 150 prevents the port 308 from connecting with a connector in this example. The angling of one or more of the ports can effectively prevent or at least hinder simultaneous use of both ports 306 and 308. The angle may prevent a user from being able to insert a cable's connector into the port 308 without first removing the test strip. The angling of the port 306 (or alternatively of the port 308) effectively prevents both ports 306 and 308 from being used simultaneously. Further, the angle between the test strip 150 and the interface 302 may prevent or hinder the user from physically contacting the port 308 while using the port 306.

Figure 14A:
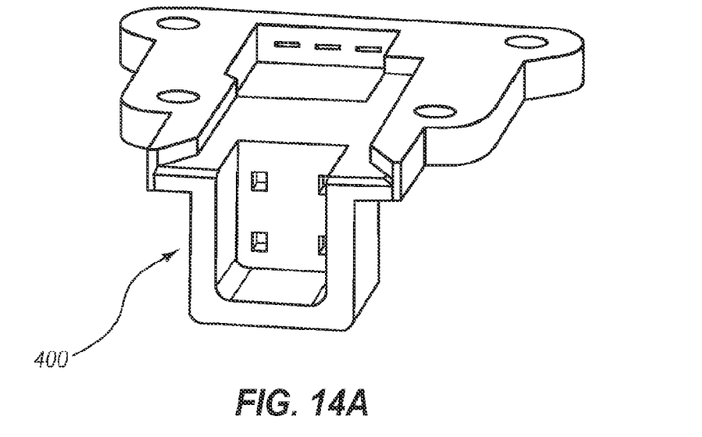
FIGS. 14A and 14B illustrate a connector that interfaces with a blood glucose port.
Figure 14B:
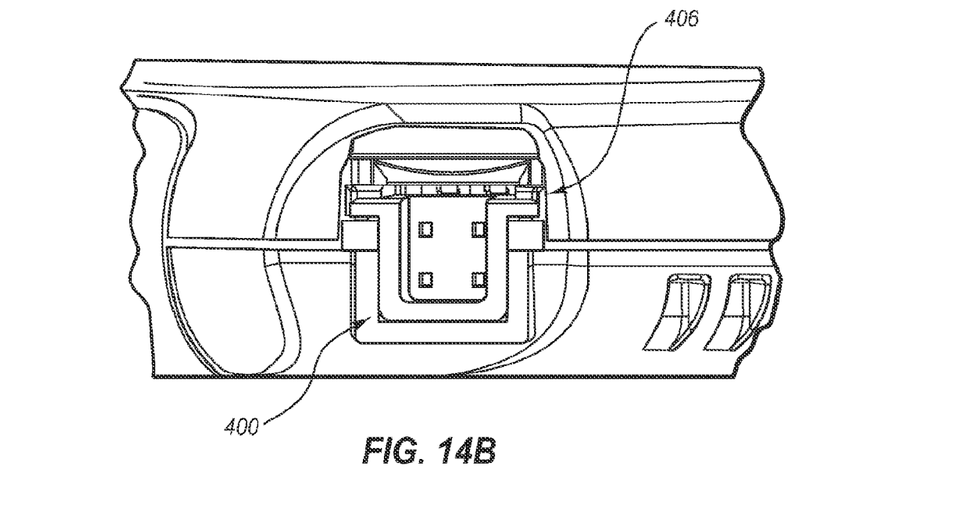

FIGS. 14A and 14B illustrate an example of a port 406 that is configured to interface with both a test strip and a cable connector. FIGS. 14A and 14B illustrate a connector 400 that interfaces with the port 406, which can also receive test strips. The connector 400 ensures that the device is used only for one function at a time. Thus, the connector 400 ensures that the device is used for analyzing a blood sample or for transferring data/charging purposes. In a certain embodiment, the port 406 is configured such that a test strip can only be inserted a particular way and such that the connector of a cable can only be inserted in a particular way. This ensures that the electrical connections used for the test strip are not inadvertently connected to the power or computer port and that the power or computer connection is not connected electrically with the circuits that are designed to interact with a test strip. Further, the port 406 may be configured such that the presence of either a test strip or a connector in the port 406 prevents, respectively, a connector or a test strip from being inserted into the port 406.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
    a body comprising a barrier with first and second surfaces, the first surface defining a cavity of a shroud;
    a connector extending through the body to the first surface of the barrier to connect to a computer port of a glucose monitoring device; and
    a plug to connect to a test strip port of the device,
    wherein at least one of the barrier or the plug prevents access to the test strip port of the device when the connector is connected to the computer port, wherein the cavity of the shroud is configured to cover the computer port and the test strip port when the connector is connected to the computer port.

2. The apparatus of claim 1, further comprising a cable connected to the connector and extending from the second surface of the barrier.

3. The apparatus of claim 2, wherein the cable is permanently connected to the connector.

4. The apparatus of claim 2, wherein the cable is detachably connected to the connector.

5. The apparatus of claim 2, wherein data is uploaded, downloaded or both to the device via the computer port of the device when the cable is connected to the computer port of the device and to a computer.

6. An apparatus, comprising:
    a body comprising a barrier with first and second surfaces, the first surface defining a cavity of a shroud;
    a connector extending through the body to the first surface of the barrier to connect to a power charging port of a glucose monitoring device; and
    a plug to connect to a test strip port of the device;
    wherein at least one of the barrier or the plug prevents access to the test strip port of the device when the connector is connected to the power charging port, wherein the cavity of the shroud is configured to cover the power charging port and the test strip port when the connector is connected to the power charging port.

7. The apparatus of claim 6, further comprising a cable connected to the connector and extending from the second surface of the barrier.

8. The apparatus of claim 7, wherein the cable is permanently connected to the connector.

9. The apparatus of claim 7, wherein the cable is detachably connected to the connector.

10. The apparatus of claim 7, wherein an internal battery of the device is configured to charge through the power charging port of the device when the cable is connected to the power charging port of the device and to a power source.

11. The apparatus of claim 10, wherein the power source is a computer.

12. A method, comprising:
    providing a glucose monitoring device having a test strip port and a computer port;
    providing an electrical protection device, wherein the electrical protection device comprises a body comprising a barrier with first and second surfaces, the first surface defining a cavity of a shroud, a connector extending through the body to the first surface of the barrier to connect to the computer port of the glucose monitoring device, and a plug to connect to the test strip port of the device, wherein at least one of the barrier or the plug prevents access to the test strip port of the device when the connector is connected to the computer port, and wherein the cavity of the shroud is configured to cover the computer port and the test strip port when the connector is connected to the computer port; and
    connecting the connector of the electrical protection device to the computer port of the glucose monitoring device.

13. The method of claim 12, wherein the electrical protection device further comprises a cable connected to the connector and extending from the second surface of the barrier.

14. The method of claim 13, wherein the cable is permanently connected to the connector.

15. The method of claim 13, wherein the cable is detachably connected to the connector.

16. The method of claim 13, further comprising uploading data, downloading data or both to the device via the computer port of the device when the cable is connected to the computer port of the device and to a computer.

17. A method, comprising:
    providing a glucose monitoring device having a test strip port and a computer port;
    providing an electrical protection device, wherein the electrical protection device comprises a body comprising a barrier with first and second surfaces, the first surface defining a cavity of a shroud, a connector extending through the body to the first surface of the barrier to connect to a power charging port of a glucose monitoring device, and a plug to connect to a test strip port of the device, wherein at least one of the barrier or the plug prevents access to the test strip port of the device when the connector is connected to the power charging port, and wherein the cavity of the shroud is configured to cover the power charging port and the test strip port when the connector is connected to the power charging port; and
    connecting the connector of the electrical protection device to the computer port of the glucose monitoring device.

18. The method of claim 17, wherein the electrical protection device further comprises a cable connected to the connector and extending from the second surface of the barrier.

19. The method of claim 17, wherein the cable is permanently connected to the connector.

20. The method of claim 17, further comprising charging an internal battery of the glucose monitoring device through the power charging port of the device when the cable is connected to the power charging port of the device and to a power source.

\* \* \* \* \*